(12) United States Patent
Merkel et al.

(10) Patent No.: US 8,648,221 B2
(45) Date of Patent: Feb. 11, 2014

(54) INTEGRATED PROCESS TO CO-PRODUCE TRANS-1-CHLORO-3,3,3-TRIFLUOROPROPENE, TRANS-1,3,3,3-TETRAFLUOROPROPENE, AND 1,1,1,3,3-PENTAFLUOROPROPANE

(75) Inventors: Daniel C. Merkel, West Seneca, NY (US); Haiyou Wang, Amherst, NY (US); Konstantin A. Pokrovski, Orchard Park, NY (US); Hsueh Sung Tung, Getzville, NY (US); Ian Shankland, Randolph, NJ (US)

(73) Assignee: Honeywell International Inc., Morristown, NJ (US)

( * ) Notice: Subject to any disclaimer, the term of this patent is extended or adjusted under 35 U.S.C. 154(b) by 26 days.

(21) Appl. No.: 13/315,341

(22) Filed: Dec. 9, 2011

(65) Prior Publication Data

US 2012/0184786 A1    Jul. 19, 2012

Related U.S. Application Data

(60) Provisional application No. 61/434,002, filed on Jan. 19, 2011.

(51) Int. Cl.
*C07C 17/23* (2006.01)

(52) U.S. Cl.
USPC ........... 570/156; 570/168; 570/164; 570/165; 570/166

(58) Field of Classification Search
None
See application file for complete search history.

(56) References Cited

U.S. PATENT DOCUMENTS

| | | | |
|---|---|---|---|
| 5,332,790 A * | 7/1994 | Bierschenk et al. | 525/331.6 |
| 6,844,475 B1 | 1/2005 | Tung et al. | |
| 7,230,146 B2 | 6/2007 | Merkel et al. | |
| 7,485,760 B2 | 2/2009 | Wang et al. | |
| 7,829,747 B2 * | 11/2010 | Wang et al. | 570/156 |
| 2005/0020862 A1 * | 1/2005 | Tung et al. | 570/164 |
| 2008/0194888 A1 | 8/2008 | Merkel et al. | |
| 2009/0043137 A1 * | 2/2009 | Wang et al. | 570/136 |
| 2010/0016457 A1 | 1/2010 | Bowman et al. | |
| 2010/0168482 A1 | 7/2010 | Rao et al. | |
| 2011/0015453 A1 | 1/2011 | Merkel et al. | |
| 2011/0201853 A1 | 8/2011 | Tung et al. | |
| 2011/0245549 A1 | 10/2011 | Merkel et al. | |

FOREIGN PATENT DOCUMENTS

| | | | | |
|---|---|---|---|---|
| EP | 0729932 A1 * | 4/1996 | | C07C 17/278 |
| EP | 729932 A1 * | 9/1996 | | |
| EP | 0939071 A1 | 9/1999 | | |
| EP | 1231195 A1 | 8/2002 | | |
| GB | 2313118 A | 11/1997 | | |
| WO | 2009003157 A1 | 12/2008 | | |

\* cited by examiner

*Primary Examiner* — Johann R Richter
*Assistant Examiner* — Medhanit Bahta
(74) *Attorney, Agent, or Firm* — Bruce O. Bradford

(57) ABSTRACT

Disclosed is an integrated process to co-produce trans-1-chloro-3,3,3-trifluoro-propene (1233zd(E)), trans-1,3,3,3-tetrafluoropropene (1234ze(E)), and 1,1,1,3,3-pentafluoropropane (245fa). Overall the co-production is a three-step process. The chemistry involves the steps of:

(1) the reaction of 240fa with anhydrous HF in excess in a liquid-phase catalyzed reactor in such a way as to co-produce primarily 1233zd(E) and 244fa (plus byproduct HCl);

(2) the 244fa stream can then be used to directly produce any of the three desired products;

(3a) the 244fa stream can be dehydrochlorinated to produce the desired second product 1234ze(E); and/or (3b) the 244fa stream can be dehydrofluorinated to produce 1233zd(E) if more of that product is desired; and/or (3c) the 244fa stream can be further fluorinated to form 245fa.

18 Claims, 1 Drawing Sheet

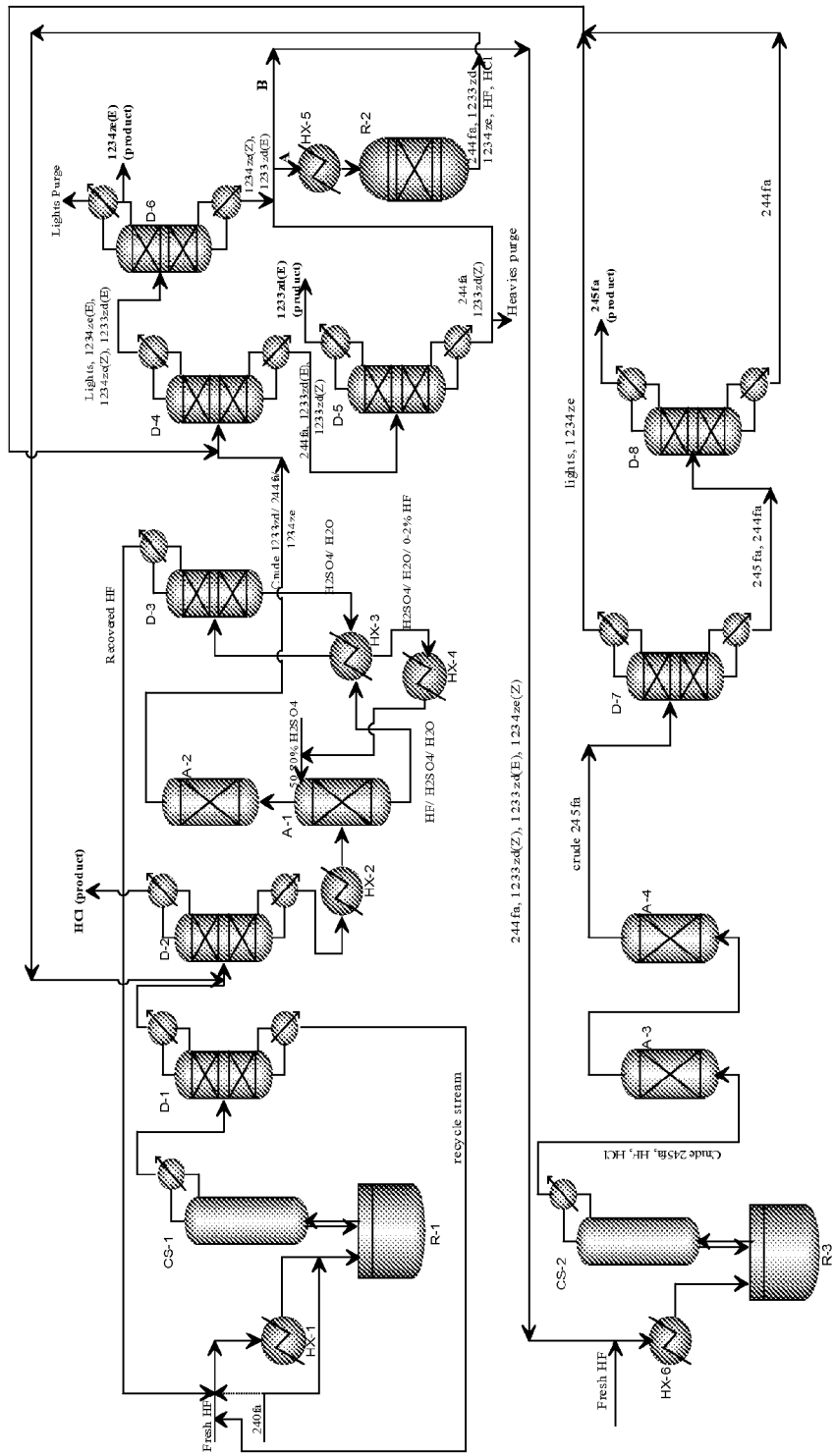

INTEGRATED PROCESS TO CO-PRODUCE TRANS-1-CHLORO-3,3,3-TRIFLUOROPROPENE, TRANS-1,3,3,3-TETRAFLUOROPROPENE, AND 1,1,1,3,3-PENTAFLUOROPROPANE

CROSS-REFERENCE TO RELATED APPLICATION

This application claims domestic priority from commonly owned, copending, U.S. Provisional Patent Application Ser. No. 61/434,002, filed Jan. 19, 2011, the disclosure of which is hereby incorporated herein by reference.

BACKGROUND OF THE INVENTION

The use of chlorofluorocarbons or hydrochlorofluorocarbons as foam-blowing agents has been banned due to concerns that their release damages the ozone layer. More recently, foam-blowing (addition of a volatile material to a polymeric mixture to cause a bubbled matrix which imparts insulation or cushioning value) has been accomplished through use of 1,1,1,3,3-pentafluoropropane (245fa); however, concern has been raised about the Global Warming Potential of this material.

Once candidate to eventually replace 245fa in these applications is trans-1-chloro-3,3,3-trifluoropropene (1233zd(E)). This material also has potential use as a solvent. See for example, U.S. Pat. No. 6,844,475, which is hereby incorporated herein by reference.

A second candidate to replace 245fa for application in single component foam blowing applications is trans-1,3,3,3-tetrafluoropropene (1234ze(E)). See for example U.S. Pat. Nos. 7,230,146 and 7,485,760, the disclosures of which are hereby incorporated herein by reference.

A process used for the production of fluoropropanes and halopropenes including 1-chloro-3,3,3-trifluoropropene (1233zd), 1,3,3,3-tetrafluoropropene (1234ze) and 245fa is taught in U.S. Patent Publication No. 2010/0168482 A1. These compounds are typically formed in a complex product mixture including other fluoropropanes and/or halopropenes in addition to reactants and other byproducts.

One problem recognized in this art has been the continued need for an economical process for the continuous preparation of 1233zd(E) and 1234ze(E). Compound 245fa will continue to be needed for some time as it is slowly phased out and new products are slowly phased in. Accordingly, the present invention provides an integrated process to co-produce these three compounds, starting from one common feed material, namely 240fa.

SUMMARY OF THE INVENTION

The present invention is directed to an integrated process to co-produce trans-1-chloro-3,3,3-trifluoro-propene (1233zd(E)), trans-1,3,3,3-tetrafluoropropene (1234ze(E)), and 1,1,1,3,3-pentafluoropropane (245fa). Overall the co-production is a three-step process. The chemistry involves the steps of:
  (1) the reaction of 240fa with anhydrous HF in excess in a liquid-phase catalyzed reactor in such a way as to co-produce primarily 1233zd(E) and 244fa (plus byproduct HCl);
  (2) the 244fa stream can then be used to directly produce any of the three desired products;
  (3a) the 244fa stream can be dehydrochlorinated to produce the desired second product 1234ze(E); and/or
  (3b) the 244fa stream can be dehydrofluorinated to produce 1233zd(E) if more of that product is desired; and/or
  (3c) the 244fa stream can be further fluorinated to form 245fa.

According to one embodiment of the present invention, 1233zd(E), 1234ze(E), and 245fa can all be co-produced in an integrated process starting with a single hydrochlorocarbon feed material, namely 240fa. One benefit of this process is that it avoids intimate contact of the compounds 1233zd(E) and 245fa, which would otherwise form an azeotropic composition that makes it impossible to separate the components using conventional separation techniques such as distillation.

The process has an economical advantage to produce 1234ze(E) over those methods previously disclosed in literature because it also uses the intermediate 1-chloro-1,3,3,3-tetrafluoropropane (244fa) as a precursor instead of 245fa. These compounds can both be produced from the same 240fa feed stock, but 245fa has an extra fluorine atom that is added to the original feed stock—which must be removed as HF to produce 1234ze(E). Thus, using 245fa to produce 1234ze(E) wastes one mole of HF per mole of 1234ze(E) produced. On the other hand, 1234ze(E) can be produced from 244fa by removing the last remaining chlorine atom (in the form of HCl) from the original feed stock.

The preferred process of the present invention also has an advantage in that it allows for great flexibility in producing different amounts of each compound by adjusting the operating conditions or concentrations of reactants and/or catalyst in the first liquid phase reactor.

The preferred integrated manufacturing process is different from prior art because it also includes the ability to recycle unreacted starting materials to maximize raw material utilization and product yields. It also provides the ability to isolate by-products that may be sold for commercial value.

BRIEF DESCRIPTION OF THE DRAWING

The FIGURE illustrates the relative positions of the seven major unit operations of a preferred manufacturing process of the present invention.

DETAILED DESCRIPTION OF THE INVENTION

It has now been found that 1234ze(E) and 245fa may be continuously and economically co-produced via an integrated manufacturing process which starts with a single chlorinated hydrocarbon, 240fa. One preferred embodiment of a fully integrated co-manufacturing process for making 1233zd(E) and 1234ze(E) is described in detail below.

Overall the co-production is a three-step process. The chemistry involves:
  (1) the reaction of 240fa with anhydrous HF in excess in a liquid-phase catalyzed reactor in such a way as to co-produce primarily 1233zd(E) and 244fa (plus byproduct HCl);
  (2) the 244fa stream can then be used to directly produce any of the three desired products;
  (3a) the 244fa stream can be dehydrochlorinated to produce the desired second product 1234ze(E); and/or
  (3b) the 244fa stream can be dehydrofluorinated to produce 1233zd(E) if more of that product is desired; and/or
  (3c) the 244fa stream can be further fluorinated to form 245fa.

Desired Reactions:
Step 1:

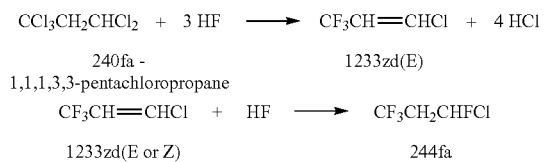

Step 2:

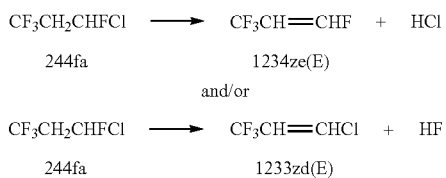

Step 3:

Major:

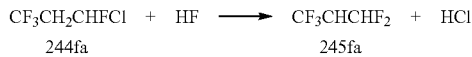

Minor (as impurities in the 244fa):

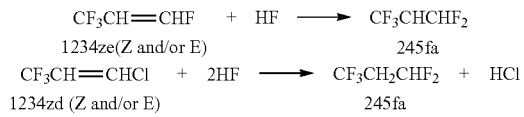

The manufacturing process preferably consists of the following seven major unit operations:
(1) Liquid phase fluorination catalyst preparation (Titanium tetrachloride);
(2) Fluorination reaction (continuous or semi-batch mode) using HF with simultaneous removal of byproduct HCl and the co-products 1233zd(E) and 244fa;
(3) Separation and purification of byproduct HCl;
(4) Separation of excess HF back to (2);
(5) Purification of final product, 1233zd(E);
(6) Dehydrochlorination of 244bb to 1234ze(E) (with recycle of HCl to recovery); and
(7) Purification of final product, 1233zd(E).
One embodiment of the relative positions of these operations is shown in the FIGURE.
Liquid Phase Fluorination Catalyst Preparation, Reactor 1

The reaction uses a liquid phase catalyst of proper strength to achieve the desired reaction; preferentially it has been found that a catalyst comprised of titanium tetrachloride (liquid under ambient conditions) which has been partially or totally fluorinated by the action of anhydrous HF, achieves the desired degree of conversion without forming undesired volatile byproducts. The catalyst fluorination is conducted by adding a specified amount of titanium tetrachloride to the agitated, temperature-controlled reactor vessel, and adding HF by a gradual flow. A moderate amount of HCl will be generated in the operation. Conditions: 10° C. to 50° C. and at about 0 to 100 psig pressure. Additional fluorination catalysts that can be used include (all are partially of totally fluorinated by the action of anhydrous HF) $SnCl_4$, $TaCl_5$, $SbCl_3$, $AlCl_3$, $SbCl_5$, alone or in combination.
Reaction and Stripping Column, Reaction 1

One key to the reaction is the equipment arrangement. An agitated, temperature-controlled reactor for the contact of both feed materials with the liquid catalyst and an integrated distillation column which permits the product to leave (along with byproduct HCl, traces of light organics, principally 1234ze(E+Z), and some anhydrous HF (AHF), while retaining the bulk of the HF, plus under-fluorinated and dimerized organics, plus the catalyst is another key. Preferably the reactor is constructed from materials which are resistant to the corrosive effects of the HF and catalyst, such as Hastelloy-C, Inconel, Monel, Incoloy, or fluoropolymer-lined steel vessels. Such liquid-phase fluorination reactors are well known in the art.

Once the catalyst has been prepared, the reaction can be initiated immediately. The flow of HF for the catalyst preparation need not be discontinued. An additional amount of HF is added to the reactor to fill the reactor to 20% to 90% of its volume while the reactor is heated to a temperature of 85° C. to 95° C. and agitated. Then the addition of the 240fa can be started immediately to cause continuous reaction while maintaining the flow of HF at an amount sufficient to produce the desired products plus an excess amount to account for losses due to azeotrope compositions of 1233zd(E)/HF and 244fa/HF that exit the top of the integrated distillation column. The reaction runs under HF rich conditions to produce the reaction co-products, 1233zd(E) and 244fa. Proper temperature control of the coolant and sufficient reflux action are necessary for the stripping column to be effective.

General operating conditions which have been found to work well for the reaction and stripping are: operating pressure of from 80 psig to 140 psig maintained by a control valve on the exiting flow from the stripper column; reactor temperature of 85° C. to 115° C., primarily supplied by steam flow into the reactor jacket; application of brine cooling to the heat exchanger on top of the stripper column to induce reflux; temperature in the center portion of the stripper about 10° C. to 40° C. below that in the reactor; additional heat input by superheating the HF vapor feed with high-pressure steam to 120° C. to 150° C.; feed rate of HF to maintain reactor and stripper conditions.
Recycle of Underfluorinated Intermediates and HF The stream exiting the stripper column (2) enters a recycle column. Here the high boiling underfluorinated intermediates and some HF are separated and returned to reactor (2) for further reaction. The crude mixture containing 1233zd/244fa, HF, and HCl is fed forward in the integrated process.
Removal of HCl The stream exiting the recycle column (3) is combined with other additional process streams that contain 1233zd/244fa/1234ze, HCl and HF (described below, see (7) and (11)). The HCl in this combined stream can then be purified and collected for sale using a low-temperature HCl distillation column. High purity HCl is isolated and can be absorbed in de-ionized water as concentrated HCl for sale.
Separation and Recycle of Excess HF Back to (2)

The bottom stream from the HCl column (4) that contains a crude product mixture of 1233zd/244fa/1234ze and about 30 wt % HF is fed to a sulfuric extractor or a phase separator for removal of HF from this mixture. HF is either dissolved in the sulfuric acid or phase separated from the organic mixture. HF is desorbed from the sulfuric acid/HF mixture by stripping distillation and recycled back to the reactor. The organic mixture either from the overhead of the sulfuric acid extractor may require treatment (scrubbing or adsorption) to remove traces of HF before it is fed to the next unit operation (6).

Purification of Final Products 1233zd(E) and 1234ze(E)

Purification of final products 1233zd(E) and 1234ze(Z) consists of three continuously operating distillation columns. The first column is used to remove light ends (including 1234ze(E)) from the crude. The light ends from the first column are fed to a second column is which 1234ze(E) is isolated in the column overhead. It should be recognized that at some point a purge of light byproducts from this stream will also be required. The third column takes the heavy ends from the first column and produces product grade 1233zd(E) as an overhead product. The third column bottoms fraction contain mostly 244fa and is combined with the bottoms of the second column. A portion of the combined stream (portion is dependant on the desired product split) is fed to a vapor phase reactor (7) and a portion is fed to a liquid phase fluorination reactor (8). It should be recognized that at some point a purge of heavy byproducts from this stream will also be required.

Dehydrohalogenation of 244fa to 1234ze(E) or 1233zd(E)

A portion of the combined streams from the bottom of the distillation columns in (6) is fed to one or more catalyzed vapor phase reactors where the 244fa is either (a) dehydrochlorinated to produce the desired 1234ze(E) product and HCl and/or (b) dehydrofluorinated to produce additional amounts of 1233zd(E) and HF.

Optionally, the reactor(s) contains both a dehydrochlorination and dehydrofluorination catalyst that produces both 1233zd(E) and 1234ze(E). The reactor effluent is recycled back to the HCl recovery column (4). Optionally, 245fa produced in (9) can also be recycled back to this step for dehydrofluorination to form 1234ze(E).

Liquid Phase Fluorination Catalyst Preparation, Reactor 2

The reaction uses a liquid phase fluorination catalyst of proper strength to achieve the desired reaction; preferentially it has been found that a catalyst comprised of antimony pentachloride (liquid under ambient conditions) which has been partially or totally fluorinated by the action of anhydrous HF achieves the desired degree of conversion without forming undesired byproducts. The catalyst fluorination is conducted by adding a specified amount of antimony pentachloride to a non-agitated, temperature-controlled reactor vessel, and adding HF by a gradual flow. A moderate amount of HCl will be generated in the operation. Conditions: reaction temperature, from 10° C. to 50° C. and from 0 psig to 100 psig pressure. Additional fluorination catalysts that can be used include in combination with antimony pentachloride (all are partially of totally fluorinated by the action of anhydrous HF) $TiCl_4$, $TaCl_5$, $SbCl_3$.

Reaction and Stripping Column, Reaction 3

One key to the reaction is the equipment arrangement. A non-agitated, temperature-controlled reactor for the contact of both feed materials with the liquid catalyst and an integrated distillation column which permits the desired 245fa product to leave, along with byproduct HCl and an amount of AHF greater than or equal to the amount needed to form an azeotrope with 245fa at the reaction pressure, while retaining the bulk of the HF, plus under-fluorinated and plus the catalyst is another key. Preferably the reactor is constructed from materials which are resistant to the corrosive effects of the HF and catalyst, such as fluoropolymer-lined steel vessels. Such liquid-phase fluorination reactors are well known in the art. Once the catalyst has been prepared, the reaction can be initiated immediately upon heating to the desired reaction temperature. The flow of HF for the catalyst preparation need not be discontinued while the reactor is heated to a temperature of 85° C. to 95° C.

Preferably the HF feed is vaporized and superheated to provide the heat necessary to maintain proper reactor operating temperatures. Then the addition of the organic mixed feed (244fa/1234ze(Z)/1233zd(Z)/1233zd(E)) can be started immediately to cause continuous reaction while maintaining the flow of HF at an amount sufficient to produce the desired product plus an excess amount to account for losses due to azeotrope compositions of 245fa/HF that exit the top of the integrated distillation column. The reaction runs under HF rich conditions to produce the reaction product, 245fa. Proper temperature control of the coolant and sufficient reflux action are necessary for the stripping column to be effective.

General operating conditions which have been found to work well for the reaction and stripping are: operating pressure of 80 psig to 140 psig maintained by a control valve on the exiting flow from the stripper column; reactor temperature of 85° C. to 115° C., primarily supplied by superheating the HF vapor feed with high-pressure steam to 120° C. to 150° C. directly into the reaction mixture and steam flow into the reactor jacket; application of brine cooling to the heat exchanger on top of the stripper column to induce reflux; temperature in the center portion of the stripper about 10° C. to 40° C. below that in the reactor; additional heat input; feed rate of HF to maintain reactor and stripper conditions.

Acid Removal

The stream exiting the stripper column (9) enters an acid removal system that consists of a water absorption column followed by a caustic absorption column followed by a drier. Here HF and HCl are removed from the 245fa crude and then the crude is dried before purification through a product absorption column and crude product recycle column. Here the high boiling underfluorinated intermediates and some HF are separated and returned to reactor (2) for further reaction. Crude 1233zd/244fa, HF, and HCl are fed forward in the integrated process.

Purification of Final Product 245fa

Purification of final product 245fa consists of two continuously operating distillation columns. The first column is used to remove light ends, mainly 1234ze(E) from the 245fa and the second column is used to remove the heavier components, primarily 244fa. The light and heavy ends that are removed from the top of the first column and bottom of the second column can both be recycled back to an earlier processing step like (4) or (6).

Integrated Process—1233zd(E), 1234ze(E), and 245fa Co-Production with HCl and Sulfuric Acid HF Recovery As shown in the FIGURE, the liquid phase reactor R1 is first charged with a fluorination catalyst selected from the group comprising $TiCl_4$, $SnCl_4$, $TaCl_5$, $SbCl_3$, $AlCl_3$, or $SbCl_5$, alone or in combination. $TiCl_4$ is most preferred. HF is first added in an amount to totally fluorinate the metal chloride catalyst; e.g., when using $TiCl_4$ a greater than 4:1 mole ratio of HF to catalyst is added. The catalyst preparation is done while the reactor is at 10° C. to 50° C. and at about 0 to 160 psig pressure. HCl is generated during catalyst preparation and can be vented out of the top of the catalyst stripper column CS-1 to control the reactor pressure at or below the intended operating pressure of the reactor. Preferably the reactor is constructed from materials which are resistant to the corrosive effects of the HF and catalyst, such as Hastelloy-C, Inconel, Monel, Incoloy, or fluoropolymer-lined steel vessels. Such liquid-phase fluorination reactors are well known in the art.

Then additional HF is continuously added into R-1 via vaporizer, HX-1, until good agitation is achieved; thereafter, this feed can be left on.

The reactor contents are then heated to about 85° C. with agitation at which point the 240fa feed is started and the fluorination reaction between 240fa and HF is initiated. Continuous 240fa is fed directly into reactor R-1 and not through heater HX-1. Optionally, 240fa is fed to reactor R-1 via HX-1.

The operating pressure of 60 psig to 160 psig (preferably 80 psig to 140 psig) is maintained by a control valve on the exiting flow from the catalyst stripper column CS-1 and the reactor temperature is kept in the range of 80° C. to 150° C., (preferably 85° C. to 115° C.) primarily supplied by steam flow into the reactor jacket. A catalyst stripper column CS-1 is connected to the reactor, R-1, and serves the purpose of knocking down and returning entrained catalyst, some HF, partially fluorinated intermediates, and some unreacted 240fa back to the reactor for further reaction.

By adjusting the operating conditions or concentrations of reactants and/or catalyst in the liquid phase fluorination reactor the reaction can be made to produce different amounts of each desired co-products 1233zd(E) and 244fa.

The stream exiting the top of catalyst stripper CS-1 consisting of unreacted 240fa, partially fluorinated intermediates and by-products, overfluorinated by-products, HF, 1233zd (E+Z), 244fa, and HCl, then enters recycle column D-1 where a stream consisting of mainly unreacted 240fa, partially fluorinated intermediates, and the majority of the HF exits the bottom of the recycle column and is recycled back to the liquid phase fluorination reactor R-1 via vaporizer HX-1.

A stream consisting of mainly 1233zd(E), 244fa, HF, and HCl exits the top of the recycle column and enters HCl column D-2. A stream consisting of mainly HCl by-product exits the top of the HCl column and is fed to an HCl recovery system. The recovered HCl by-product can be sold for profit. The HCl column bottoms consisting mainly of HF, 1233zd (E), and 244fa are then fed into an HF recovery system.

The HF recovery system starts with the crude 1233zd/244fa/HF stream being vaporized in heat exchanger HX-2 and fed into HF absorption column A-1. Here a liquid stream of 50% to 80% $H_2SO_4$ contacts the gaseous 1233zd/HF stream and absorbs the majority of the HF. The stream exiting the bottom of A-1 consists of $HF/H_2SO_4/H_2O$ and is fed to heat exchanger HX-3 where it is heated to a temperature sufficient to flash the majority of the HF along with small amounts of $H_2O$ and $H_2SO_4$. This stream is fed to HF recovery distillation column D-3. The liquid remaining after the HF is flashed off in HX-3 consisting mainly of $H_2SO_4$ and $H_2O$ (with 0% to 2% HF) is cooled in HX-4 and recycled back to HF absorption column A-1.

The HF recovery column, D-3, bottoms stream consisting of mainly $H_2SO_4$ and $H_2O$ are recycled back to heat exchanger HX-3 Anhydrous HF is recovered from the top of the HF recovery column, D-3, and is recycled back to the reactor R-1 via vaporizer are HX-1. The stream exiting the top of HF absorption column A-1 consisting of mainly 1233zd(E) and 244fa (trace HF) is sent forward to a polishing system A-2 where the gaseous stream contacts a water or a caustic solution to remove trace HF and is subsequently dried with a desiccant. Acid free crude product exiting absorber A-2 is sent to the first of three purification columns, D-4.

A stream exiting the top of the column D-4 consists mainly of 1234ze(E) and reaction bi-products that have boiling points lower than that of 1233zd(E) is fed to1234ze(E) product recovery distillation column D-6. Product grade 1234ze (E) exits the top of distillation column D-6 to product storage. The 1234ze(E) product recovery column's bottoms stream consists mainly of 1234ze(Z) and 1233zd(E) (possibly with a small amount of 245fa). This bottoms stream is combined with the bottoms stream from the 1233zd(E) product recovery column D-5 (further described below).

This combined stream is then split into two separate streams A and B, the ratio of which is determined by the desired product distribution. Stream A is fed to vaporizer HX-5 and then to vapor phase dehydrohalogenation/isomerization reactor R-2. Any 245fa impurity will dehydrofluorinate in R-2 to produce the desired 1234ze(E) product. In addition, the 1234ze(Z) impurity will isomerize in R-2 to produce the desired 1234ze(E) product. Stream B's fate is described below.

The vapor phase dehydrochlorination catalysts employed in R-2 may be metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^-$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Incoloy 825, Inconel 625, Inconel 600, and Inconel 625.

Preferred catalysts include activated carbon, stainless steel (e.g., SS 316), austenitic nickel-based alloys (e.g., Inconel 625), nickel, fluorinated 10% CsCl/MgO, and 10% CsCl/$MgF_2$. The reaction temperature is preferably about 300° C. to 550° C. and the reaction pressure is preferably from 0 psig to about 150 psig.

The reactor effluent from R-2 is recycled back to HCl recovery distillation column, D-2 where the HCl is recovered.

Optionally, Stream A can be fed into a liquid phase stirred reactor along with a caustic solution to dehydrohalogenate 244fa (major) and 245fa (minor) and produce both desired products 1234ze(E) and 1233zd(E) as some of the 244fa will dehydrochlorinate and some will dehydrofluorinate.

The stream exiting the bottom of column D-4, consisting mainly of 1233zd(E+Z), 244fa and heavier bi-products, is fed to 1233zd(E) product recovery distillation column D-5. Product grade 1233zd(E) exits the top of distillation column D-5 to product storage. The 1233zd(E) product column's bottoms stream consist mainly of 244fa, 1233zd(Z) and reaction bi-products with boiling points higher than that of 1233zd(E). This bottoms stream, after combination with the bottoms stream from 1234ze(E) product recovery column D-6, is then split into two separate streams A and B, as described above. The 1233zd(Z) impurity will to some extent isomerize in R-2 to produce the desired 1233zd(E) product.

Liquid phase reactor R-3 is first charged with fluorination catalyst alone or in combination from the group comprising $SbCl_5$, $TiCl_4$, $SnCl_4$, $TaCl_5$, $SbCl_3$, or $AlCl_3$, alone or in combination. $SbCl_5$ is most preferred. HF is first added in an amount to at least partially fluorinate the metal chloride catalyst; e.g., when using $SbCl_5$ a greater than 3:1 mole ratio of HF to catalyst is added. The catalyst preparation is done while the reactor is at 10° C. to 50° C. and at from 0 psig to about 160 psig pressure.

HCl is generated during catalyst preparation and can be vented out of the top of the catalyst stripper column CS-1 to control the reactor pressure at or below the intended operating pressure of the reactor. Preferably the reactor is constructed from materials which are resistant to the corrosive effects of the HF and catalyst, such as a fluoropolymer-lined steel vessels. Such liquid-phase fluorination reactors are well known in the art.

Additional HF is continuously added into R-3 via vaporizer, HX-9, and the reactor is heated until the desired reaction temperature of about 90° C. is achieved, at which point Stream B is combined with the fresh HF before HX-9 and then into R-3 where the fluorination reaction between HCFC-244fa (major), 1234ze(E) (minor), 1233zd(Z) (minor), and 1233zd(E) (minor) and HF is initiated.

The operating pressure of 60 psig to 160 psig (preferably 80 psig to 140 psig) is maintained by a control valve on the exiting flow from the catalyst stripper column CS-1 and the reactor temperature is kept in the range of 80° C. to 150° C., (preferably 85° C. to 115° C.) primarily supplied by superheated HF feed and steam flow into the reactor jacket. A catalyst stripper column CS-1 is connected to the reactor, R-3, and serves the purpose of knocking down and returning entrained catalyst, some HF, partially fluorinated intermediates, and some unreacted 244fa, back to the reactor for further reaction.

The stream exiting the top of catalyst stripper CS-1 consisting mainly of 245fa, HF, HCl, and unreacted starting organic materials then enters water absorption column A-3 where most of the HF and HCl are removed. The aqueous stream exiting the bottom of the water absorber A-3 is neutralized and disposed of as waste. The stream exiting the top of the water absorber column A-3 consisting of mainly 245fa and unreacted starting organic materials (trace HF and HCl) is sent forward to a polishing system A-4 where the gaseous stream contacts a weak caustic solution to remove trace HF and HCl and is subsequently dried with a desiccant.

Acid free crude product exiting absorber A-4 is sent to the first of two purification columns, D-7. A stream exiting the top of the column D-7 consists mainly of 1234ze(E) and reaction bi-products that have boiling points lower than that of 245fa is recycled back to D-4 and the column bottoms are fed to 245fa product recovery distillation column D-8. Product grade 245fa exits the top of distillation column D-8 to product storage. 244fa and reaction bi-products that have boiling points higher than that of 245fa are recycled back to D-4.

EXAMPLE 1

This example illustrates the continuous reaction where 240fa is continuously fed into a charge of titanium halide catalyst and HF.

A clean, empty 10-gallon jacketed, agitated reactor of Hastelloy C construction was prepared. This reactor was connected to a two-inch diameter vertical, PTFE-lined pipe containing packing material (stripper), which is in turn connected to an overhead heat exchanger. The heat exchanger was supplied with −40° C. brine circulation on the shell side. Vapors exiting this stripper were processed through a scrubber, in which temperature-controlled dilute potassium hydroxide aqueous solution was circulated. Vapors exiting this stripper were collected in a weighed, chilled (−40° C.) cylinder, followed by a smaller cylinder in series chilled in a dry ice bath.

Initially about 1200 grams lbs of $TiCl_4$ was added as a catalyst, followed immediately by 28 lbs of HF. The reactor contents were heated to about 85° C. while agitated and was at a pressure of 120 psig after formation of HCl after catalyst fluorination. The HF feed to the reactor was continued at a rate of 1 lb/hr after being vaporized through a steam heated exchanger. Then a continuous feed of 240fa was started at 1.0 lb/hr. The reactor was kept at 85° C. to 87° C. and at a pressure of 120 psig. Samples of the organic portion of the reactor effluent exiting the top of the catstripper were analyzed using a GC. Results showed about a 55 GC area % of 244fa and about 42 GC area % 1233zd(E). The reactor ran continuously for 56 hours at these conditions with very consistent results.

EXAMPLE 2

This example illustrates the semi-batch reaction where 240fa is continuously fed into a charge of titanium halide catalyst and HF.

The same reactor as in Example 1 was used. The reactor was charged with 2600 grams of fresh $TiCl_4$ catalyst. The intent of the experiment was actually to produce 1233zd(E) with high selectivity.

The process (reaction of 240fa+HF in the presence of $TiCl_4$ catalyst) was changed from a completely batch process to a semi-continuous process with the hopes of reducing the residence time of the G240 in the reactor and thereby reducing the formation of the over fluorinated species, 244fa. The reactor was initially charged with 50 lbs of HF followed by 13 lbs of G240 and. The reactor temperature was slowly increased and reaction was observed at about 80° C. to 85° C. The reaction was allowed to proceed for a couple of hours with the lighter components continuously being taken overhead of the catstripper to the scrubber and product collection dry ice traps (DITs). The 240fa feed was then started continuously and added into the vapor space of the reactor. The overhead take-off system was modified so that a constant amount of material was taken off the catstripper and the G240 feed rate was adjusted to match that rate. Several times during the production run the reactor was shutdown to add more HF and started up again as before.

The selectivity of the reaction for producing 1233zd was surprisingly low at 40% to 50%. The major by-product was the over fluorinated species 244fa (50% to 55%). Running HF rich and a larger amount of catalyst adversely affected the selectivity to 1233zd(E).

EXAMPLE 3

This example (called Run #3) illustrates the semi-batch reaction where HF was continuously fed into a charge of titanium tetrachloride catalyst and 240fa.

A clean, empty 10-gallon jacketed, agitated reactor of Hastelloy C construction was prepared. This reactor was connected to a 2 inch diameter vertical, PTFE-lined pipe containing packing material (stripper), which was in turn connected to an overhead heat exchanger. The heat exchanger was supplied with −40° C. brine circulation on the shell side. Vapors exiting this stripper were processed through a scrubber, in which temperature-controlled dilute potassium hydroxide aqueous solution was circulated. Vapors exiting this stripper were collected in a weighed, chilled (−40° C.) cylinder referred to as the product collection cylinder, followed by a smaller cylinder in series chilled in a dry ice bath.

For Run #3, 14 lbs of anhydrous HF was fed to assure catalyst fluorination. Next, 1.5 lbs of $TiCl_4$ was added as a catalyst. HCl was immediately generated as observed by the build-up of pressure in the reactor. After the pressure was reduced by venting most of the HCl from the system, 50 lbs of 240fa was added. The reactor was heated. At about 85° C. HCl started to be generated indicating that the fluorination reaction was initiated. The system pressure was controlled at about 120 psig. Additional HF was then fed continuously and product was collected in the product collection cylinder until the 240fa was consumed. The GC analysis of the crude material collected during the run was as follows: 86.4% 1233zd (E); 5.5% G-244fa; 3.1% 1234ze(E); 1.5% 1233zd(Z); 1.1% 1234ze(Z); 1.1% dimmer; and 0.2% trifluoropropyne.

EXAMPLE 4

244fa Dehydrohalogenation Over Metal Chloride Catalysts

In this example a series of mono-, bi-, and tri-valent metal chlorides were used as dehydrohalogenation catalysts. 20 ml of catalyst was used. 244fa was passed over each catalyst at a rate of 12 g/h at a temperature of 350° C. As shown below in Table 1, all the mono- and bi-valent metal chloride catalysts provided a trans/cis (t/c)-1234ze selectivity higher than 80% and a t/c-1233zd selectivity lower than 20%, indicating these catalysts are more active for 244fa dehydrochlorination than its dehydrofluorination. In comparison, the mono-valent metal chloride catalysts are more selective to form t/c-1234ze than bi-valent metal chloride ones.

A 244fa conversion higher than 90% was achieved over the following catalysts: 10.0 wt % LiCl/C, 10.0 wt % KCl/C, and 10.0 wt % MgCl$_2$/C. On the other hand, the tri-valent iron chloride catalyst exhibited a t/c-1234ze selectivity of about 9% and a t/c-1233zd selectivity of about 61%, which suggests that this catalyst is more active for 244fa dehydrofluorination than its dehydrochlorination.

TABLE 1

244fa dehydrohalogenation over metal chloride catalysts at 350° C.

| Catalyst | Conversion, % 244fa | Selectivity, % | | | |
|---|---|---|---|---|---|
| | | t/c-1234ze | 245fa | t/c-1233zd | Others |
| 10.0 wt % LiCl/C | 96.2 | 95.2 | 0.0 | 4.4 | 0.4 |
| 10.0 wt % KCl/C | 97.9 | 94.4 | 0.0 | 4.9 | 0.7 |
| 10.0 wt % MgCl$_2$/C | 99.3 | 92.9 | 0.0 | 6.7 | 0.4 |
| 10.0 wt % NiCl$_2$/C | 89.3 | 93.4 | 0.0 | 5.4 | 1.2 |
| 10.0 wt % CuCl$_2$/C | 28.5 | 83.8 | 0.0 | 13.0 | 3.2 |
| 10.0 wt % ZnCl$_2$/C | 29.4 | 80.8 | 1.0 | 17.0 | 1.2 |
| 10.0 wt % FeCl$_3$/C | 66.8 | 9.4 | 24.3 | 61.4 | 4.9 |

EXAMPLE 5

244fa Dehydrohalogenation Over Alkaline Metal Chloride-Doped MgF$_2$ Catalysts

In this example a series of alkaline metal chloride-doped MgF$_2$ catalysts are used as dehydrohalogenation catalysts. 20 ml of catalyst is used. 244fa is passed over each catalyst at a rate of 12 g/h at a temperature of 350° C. As shown below in Table 2, all the alkaline metal chloride-doped MgF$_2$ catalysts provide a t/c-1234ze selectivity higher than 90% and a t/c-1233zd selectivity lower than 5%, indicating these catalysts are much more active for 244fa dehydrochlorination than its dehydrofluorination.

TABLE 2

Reactivity of alkaline metal chloride-doped MgF$_2$ catalysts during 244fa dehydrohalogenation at 350° C.

| Catalyst | Conversion, % 244fa | Selectivity, % | | | |
|---|---|---|---|---|---|
| | | t/c-1234ze | 245fa | t/c-1233zd | others |
| 10 wt % LiCl/MgF$_2$ | 42.9 | 90.5 | 0.0 | 4.8 | 4.7 |
| 10 wt % KCl/MgF$_2$ | 47.1 | 95.8 | 0.0 | 0.7 | 3.5 |
| 10 wt % CsCl/MgF$_2$ | 51.4 | 97.0 | 0.0 | 0.0 | 3.0 |

EXAMPLE 6

This example illustrates the recovery of anhydrous HF from a mixture of HF, 1233zd, and 244fa according to certain preferred embodiments of the present invention.

A mixture consisting of about 30 wt. % 1233zd(E), 40 wt. % 244fa, and about 30 wt. % HF is vaporized and fed to the bottom of a packed column at a feed rate of about 2.9 lbs per hour for about 4 hours. A stream of about 80 wt. % sulfuric acid (80/20 H$_2$SO$_4$/H$_2$O) with about 2% HF dissolved therein is fed continuously to the top of the same packed column at a feed rate of about 5.6 lbs per hour during the same time frame. A gaseous stream exiting the top of the column comprises 1233zd(E) and 244fa with less than 1.0 wt. % HF therein. The concentration of HF in the sulfuric acid in the column bottoms increases from 2.0 wt. % to about 15 wt. %.

The column bottoms containing sulfuric acid and about 15 wt. % HF is collected and charged into a two gallon PTFE vessel. The mixture is heated to about 140° C. to vaporize and flash off HF product, which is collected. The collected HF product contains about 6000 ppm water and 500 ppm sulfur. The sulfuric acid contains about 500 ppm of TOC (total organic carbon).

The HF collected from flash distillation is distilled in a distillation column and anhydrous HF is recovered. The recovered anhydrous HF contains less than 50 ppm of sulfur impurities and lees than 100 ppm water

EXAMPLE 7

This example demonstrates the purification of the acid free 1233zd(E) crude product. This is distillation column D-5 in FIG. 1. 92 lbs of acid free 1233zd/244fa crude material produced in Example 2 was charged to a batch distillation column. The crude material contained about 94 GC area % and 6 GC area % impurities. The distillation column consisted of a 10 gallon reboiler, two inch ID by ten feet long propack column, and a shell and tube condenser. The column had about 30 theoretical plates. The distillation column was equipped with temperature, pressure, and differential pressure transmitters. About 7 lbs of a lights cut was recovered which consisted of mainly 1234ze(Z+E), trifluoropropyne, 245fa, and 1233zd(E). 82 lbs of 99.8+ GC area % 1233zd(E) were collected. The reboiler residue amounting to about 3 lbs was mainly 244fa, 1233zd(Z), 1233zd dimmer, and 1233zd (E). The recovery of 99.8+ GC area % pure 1233zd(E) was 94.8%.

EXAMPLE 8

This example demonstrates the use of the recycle column. A representative 1233zd(E) and 244fa liquid phase reactor effluent mixture as determined in Example 2 is charged into a batch distillation column. The distillation column consists of a 10 gallon reboiler, two inch ID by ten feet long propack column, and a shell and tube condenser with −40° C. coolant flow capability. The column has about 30 theoretical plates. The distillation column is equipped with temperature, pressure, and differential pressure transmitters. The distillation column feed mixture is about 30 wt % HF, 37 wt % HCl and 33% 1233zd(E)/244fa crude. The distillation is run at a pressure of about 100 psig and a differential pressure (delta P) of 15-20 inches of water.

Both the distillate and reboiler are sampled periodically and analyzed for organic, HF, and HCl using gas and ion chromatography. Initially, HCl, organic, and HF are observed in both samples. As more material is removed as distillate the concentration of the reboiler changes. First, the concentration of HCl decreases until it is undetectable. The distillation is allowed to proceed until the concentration of organic in the reboiler sample decreases to only trace amounts as analyzed using gas chromatography. At the conclusion of the distillation the material remaining in the reboiler is essentially pure HF. The recovered HF (reboiler bottoms) is then used to demonstrate recycle of recovered HF back to the liquid phase fluorination reactor and works satisfactorily.

EXAMPLE 9

This example illustrates continuous distillation of the crude mixture consisting essentially of 1234ze(E), 1234ze (Z), and 245fa. The distillation column consisted of a 10 gallon reboiler, two inch ID by ten feet long propack column, and a shell and tube condenser. The column had about 30 theoretical plates. The distillation column was equipped with reboiler level indicator; temperature, pressure, and differential pressure transmitters. The distillation was run at pressure of about 50 psig and differential pressure of about 17 inches of $H_2O$ in the continuous mode.

The feed consisting essentially of 1234ze(E), 1234ze(Z), 245fa, and small amount of impurities (see Table 3) was continuously feed via the inlet port at the bottom of the distillation column at the rate of about 1.75 lb/hr. The distillate consisting essentially of 1234ze(E) and light impurity (see Table 3) was collected from the top of the condenser at the rate of about 1.02 lb/hr. The stream consisting essentially of 245fa and 1234ze(Z) (see Table 3) was continuously taken out from the bottom of reboiler at the rate of about 0.73 lb/hr in order to maintain the level of material in the reboiler at about 40%. The distillation was run continuously for about 1000 hours.

TABLE 3

Composition of 1234ze(E) distillation column streams

| | 3,3,3-trifluoropropyne Wt. % | 1234ze(E) Wt. % | 1234ze Wt. % | 1234ze(Z) Wt. % | 1233zd Wt. % | 245fa Wt. % |
|---|---|---|---|---|---|---|
| Feed composition | 0.0263 | 58.1003 | 0.0253 | 11.3939 | trace | 30.4542 |
| Distillate composition | 0.0497 | 99.9503 | 0.0000 | — | — | — |
| Bottoms composition | — | 0.0801 | 0.0604 | 27.1886 | trace | 72.6709 |

EXAMPLES 10 AND 11

Examples for 244fa Dehydrohalogenation to t/c-1234ze and t/c-1233zd

In Example 10, fluorinated $Cr_2O_3$ was used as a dehydrohalogenation catalyst. 20 ml of catalyst was charged into a ¾-inch Monel reactor. 244fa feed was passed through the catalyst at a rate of 12 grams/hour at a temperature of 350° C.

As shown below in Table 4, the fluorinated $Cr_2O_3$ catalyst provided a 1233zd selectivity of about 75% and a 1234ze selectivity of about 21%, indicating 1234ze and 1233zd can be co-produced from 244fa dehydrohalogenation over this catalyst. All 244fa was converted during the reaction.

TABLE 4

244fa dehydrohalogenation over a fluorinated metal oxide catalyst at 350° C.

| | | Selectivity (%) | | | |
|---|---|---|---|---|---|
| Catalyst | 244fa conv. (%) | t/c-1234ze | 245fa | t/c-1233zd | Others |
| Fluorinated $Cr_2O_3$ | 100.0 | 20.7 | 0.0 | 74.6 | 4.7 |

In Example 11, aluminum fluoride was used as dehydrohalogenation catalyst. 20 ml of catalyst was charged into a ¾-inch Monel reactor. 244fa feed was passed through each catalyst at a rate of 12 grams/hour at a temperature of 350° C.

As shown below in Table 5, the $AlF_3$ catalyst provided a 1233zd selectivity of about 77% and a 1234ze selectivity of about 22%, indicating 1234ze and 1233zd can be co-produced from 244fa dehydrohalogenation over this catalyst. All 244fa was converted during the reaction.

TABLE 5

244fa dehydrohalogenation over a metal halide catalyst at 350° C.

| | | Selectivity (%) | | | |
|---|---|---|---|---|---|
| Catalyst | 244fa conv. (%) | t/c-1234ze | 245fa | t/c-1233zd | others |
| $AlF_3$ | 100.0 | 21.8 | 0.0 | 77.3 | 0.9 |

EXAMPLE 12

This example demonstrates the dehydrohalogenation of 244fa in a caustic solution to produce both 1234ze(E) and 1233zd(E). 539.5 grams of 9.3 wt % KOH solution and 135.4 grams of 90.0 GC area % pure 244fa were added to a 1.0 liter stainless steel (SS) cylinder. The other major component was 1223xd which amounted to 9.2 GC area %. The cylinder was heated to 75° C. to 80° C. and shaken for five (5) hours. A sample of the vapor space showed the presence of 75.6 area % 1234ze trans isomer, 12.9 area % 1234ze cis isomer, 8.5 GC area % 244fa, and 0.8 GC area % 1223xd. A sample of the organic liquid phase showed 24.4 GC area % 1234ze(E), 12.9 GC area % 1233zd(E) isomer, 44.2 GC area % 244fa, and 8.1 GC area % 1223xd.

560.0 grams of aqueous solution was collected after the experiment which amounts to a weight gain of 20.5 grams in the aqueous layer. Assuming this weight gain is HCl that was produced during the dehydrochlorination of 244fa it can be calculated that about a 60% conversion of 244fa to 1234ze occurred during the reaction.

EXAMPLE 13

A continuous liquid phase fluorination of a mixed stream containing 244fa, 1233zd(Z), 1233zd(E), and 1234ze(Z) is demonstrated. The fluorination catalyst for the experiment is $SbCl_5$. 6500 grams of $SbCl_5$ are contained in a PTFE-lined liquid phase reactor equipped with a catalyst stripper, two-inch ID (inside diameter) packed column and with a condenser whose function is to return entrained catalyst, some of the unreacted HF and some of the unreacted organic back to the reactor when the system is running in continuous reaction mode. The reactor is 2.75-inch ID×36-inch L (length) and is not equipped with a mixer/agitator. The reactor is heated to about 85° C. to 87° C. The catalyst is then activated by the addition of 1500 grams of HF followed by 1500 grams of $Cl_2$. HCl generated by the fluorination of the catalyst raises the reaction system pressure to about 100 psig where it is controlled.

The continuous gaseous HF feed is started first. It is bubbled into the liquid catalyst through a dip tube at a rate of 1.9 lb/hr, and when 1.0 lb of HF has been added, the mixed organic feed stream is introduced. It also enters the liquid catalyst by way of a dip tube and consist of about 83% 244fa, 10% 1234ze(Z), 5% 1233zd(Z), and 2% 1233zd(E). The mixed organic is fed continuously at rate of 2.0 lb/hr. The mole ratio of HF to organic raw material is 7:1. The reaction temperature is maintained at 90° C. to 95° C. and the pressure is maintained at 120 psig. 245fa, unreacted organic, organic by-products, HCl, and unreacted HF exit the top of the cat-stripper column. The experiment is run continuously for over 500 hours and the average conversion of the organic raw material is greater than 99.5% while the selectivity to 245fa reaches 99.5%. $Cl_2$ (0.02 mole/mole organic) is continuously fed into the reaction mixture on a periodic basis through a dip tube in order to keep the catalyst active.

EXAMPLE 14

245fa crude material exiting a 50 gallon pilot plant fluorination reaction system was contacted with water in an absorption column to remove HCl and HF. Only a trace amount of acid remained. This stream was then contacted by a dilute caustic stream in a second absorber removing the remaining acid. The stream was then passed through a column containing X13 molecular sieves to remove any moisture that was added to the stream during contact with water during the acid removal step.

EXAMPLE 15

The dried and acid free 245fa crude material from Example 13 was then distilled continuously to greater than 99.95% purity using a series of two conventional distillation columns to remove most of the low and high boiling impurities.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An integrated process to co-produce trans-1-chloro-3,3,3-trifluoropropene (1233zd(E)), trans-1,3,3,3-tetrafluoropropene (1234ze(E)), and 1,1,1,3,3-pentafluoropropane (245fa) comprising the steps of:
    (1) reacting 1,1,1,3,3-pentachloropropane (240fa) with HF in a liquid-phase catalyzed reactor wherein the catalyst comprises $TiCl_4$ so as to co-produce at least 40% 1233zd (E), and at least 5% 3-chloro-1,1,1,3-tetrafluoro-propane (244fa), plus byproduct HCl;
    (2) further reacting the 244fa product stream as follows:
    (3a) the 244fa stream is dehydrochlorinated to produce 1234ze(E); and
    (3b) the 244fa stream is dehydrofluorinated to produce 1233zd(E); and
    (3c) the 244fa stream is further fluorinated to produce 245fa.

2. The process of claim 1, wherein the 244fa stream is dehydrochlorinated to produce 1234ze(E).

3. The process of claim 1, wherein the 244fa stream is dehydrofluorinated to produce 1233zd(E).

4. The process of claim 1, wherein the 244fa stream is further fluorinated to produce 245fa.

5. The process of claim 1, wherein the step (1) fluorination reaction is conducted in a continuous mode with simultaneous removal of the byproduct HCl and separation of the 1233zd(E) and 244fa.

6. The process of claim 1, wherein the step (1) fluorination reaction is conducted in a batch mode with removal of the byproduct HCl and separation of the 1233zd(E) and 244fa.

7. The process of claim 1, wherein step (3b) is a vapor phase reaction using a dehydrofluorination catalyst.

8. The process of claim 7, wherein the dehydrofluorination catalyst is selected from the group consisting of fluorinated metal oxides, metal fluorides, and supported metal catalysts.

9. The process of claim 7, wherein the dehydrofluorination catalyst is fluorinated $Cr_2O_3$.

10. The process of claim 1, further comprising one or more purification steps to recover the 1233zd(E), 245fa, and 1234ze(E) products.

11. The process of claim 6, which further includes HCl recovery.

12. The process of claim 11, which further includes an HF recycle step.

13. The process of claim 12, which further includes recycle of unreacted 244fa to step (2) of the process.

14. An integrated process to co-produce trans-1-chloro-3,3,3-trifluoropropene (1233zd(E)), and one or both of trans-1,3,3,3-tetrafluoropropene (1234ze(E)), and 1,1,1,3,3-pentafluoropropane (245fa), comprising the steps of:
    (1) reacting 1,1,1,3,3-pentachloropropane (240fa) with HF in a liquid-phase catalyzed reactor wherein the catalyst comprises TiCl$_4$ so as to co-produce at least 40% 1233zd(E) and 3-chloro-1,1,1,3-tetrafluoropropane (244fa), plus byproduct HCl; and (2) further reacting the 244fa product stream with one or more of the following reactions:

(3a) the 244fa stream is dehydrochlorinated to produce 1234ze(E);

(3b) the 244fa stream is dehydrofluorinated to produce 1233zd(E);

(3c) the 244fa stream is further fluorinated to produce 245fa.

15. The process of claim 14, wherein the 244fa stream is dehydrochlorinated to produce 1234ze(E).

16. The process of claim 14, wherein the 244fa stream is dehydrofluorinated to produce 1233zd(E).

17. The process of claim 14, wherein the 244fa stream is further fluorinated to produce 245fa.

18. The process of claim 14, which further includes recycle of unreacted 244fa to step (2) of the process.

* * * * *